United States Patent [19]
Kawano et al.

[11] Patent Number: 5,990,183
[45] Date of Patent: Nov. 23, 1999

[54] POROUS PARTICLES, POROUS HOLLOW PARTICLES AND METHOD OF PREPARING SUCH PARTICLES

[75] Inventors: Yoshinobu Kawano, Miyazaki; Yasuo Hatate, Kogoshima; Toru Taniguchi, Tokyo, all of Japan

[73] Assignee: Reika Kogyo Kabushiki Kaisha, Tokyo, Japan

[21] Appl. No.: 08/806,340

[22] Filed: Feb. 26, 1997

[30]     Foreign Application Priority Data

| Feb. 26, 1996 | [JP] | Japan | 8-063711 |
| Mar. 7, 1996 | [JP] | Japan | 8-050629 |
| May 24, 1996 | [JP] | Japan | 8-129690 |

[51] Int. Cl.$^6$ ........................................................ C08J 9/28
[52] U.S. Cl. ........................................... 521/64; 521/65
[58] Field of Search ........................................ 521/64, 65

[56]     References Cited

U.S. PATENT DOCUMENTS

| 3,255,127 | 6/1966 | Von bonin | 521/64 |
| 3,442,842 | 5/1969 | Von Bonin | 521/64 |
| 3,879,314 | 4/1975 | Gunning et al. | 521/64 |
| 4,137,380 | 1/1979 | Gunning et al. | 521/64 |
| 4,321,332 | 3/1982 | Beresford et al. | 521/64 |
| 4,461,849 | 7/1984 | Karickoff | 521/64 |
| 4,808,633 | 2/1989 | Ferguson et al. | 521/64 |
| 4,826,881 | 5/1989 | Ferguson et al. | 521/64 |
| 5,470,887 | 11/1995 | Perrins et al. | 521/65 |

FOREIGN PATENT DOCUMENTS

| 3637057 | 10/1986 | Germany | C08F 8/00 |
| 1-207133 | 8/1989 | Japan . | |
| 3-11282 | 2/1991 | Japan | C08F 2/32 |

*Primary Examiner*—Morton Foelak
*Attorney, Agent, or Firm*—Fish & Richardson P.C.

[57]     ABSTRACT

A first dispersion phase is dispersed in a first continuous phase comprising a solidifying component so as to prepare a primary emulsion, and this primary emulsion s ispersed in a second continuous phase as a second dispersion phase so as to prepare a secondary emulsion. The solidifying component in the secondary emulsion is then solidified, and the first dispersion phase is removed leaving pores so as to form porous particles.

20 Claims, 6 Drawing Sheets

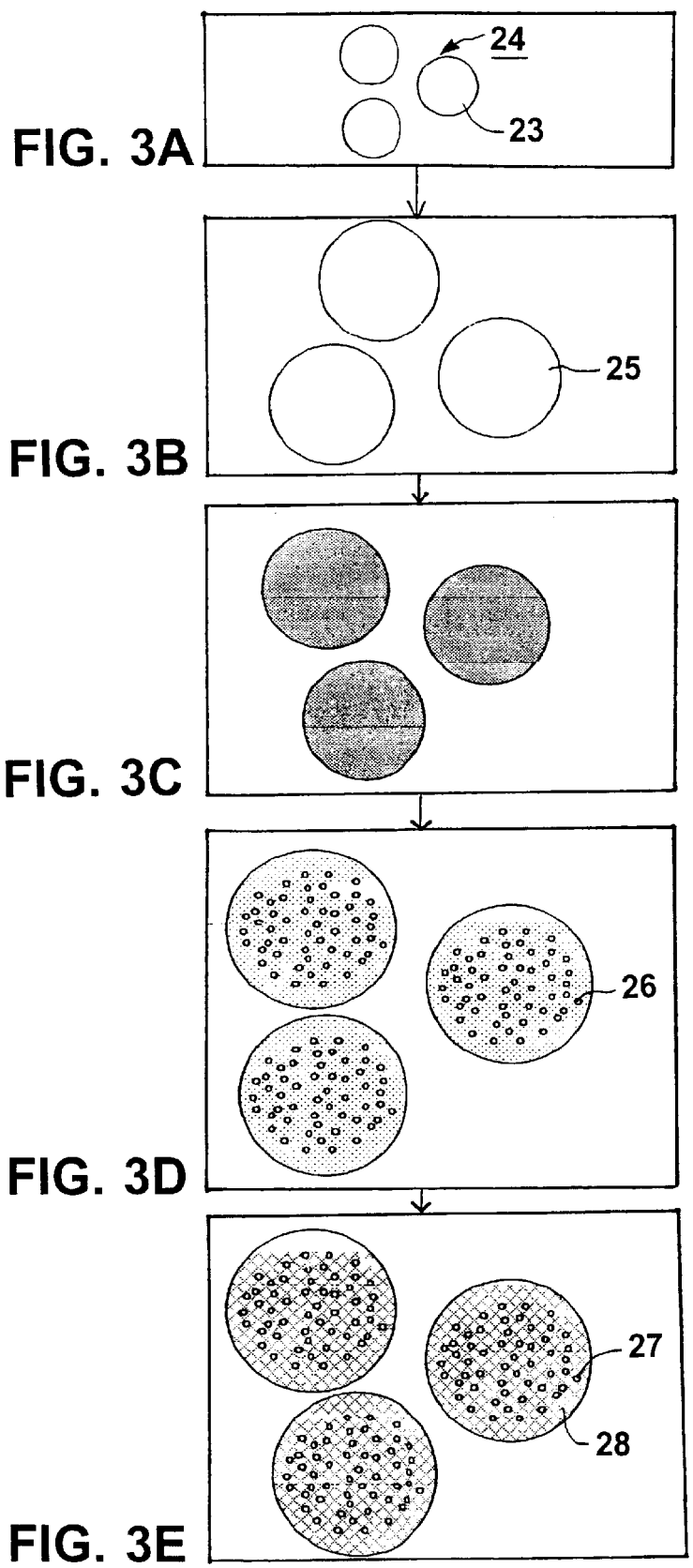

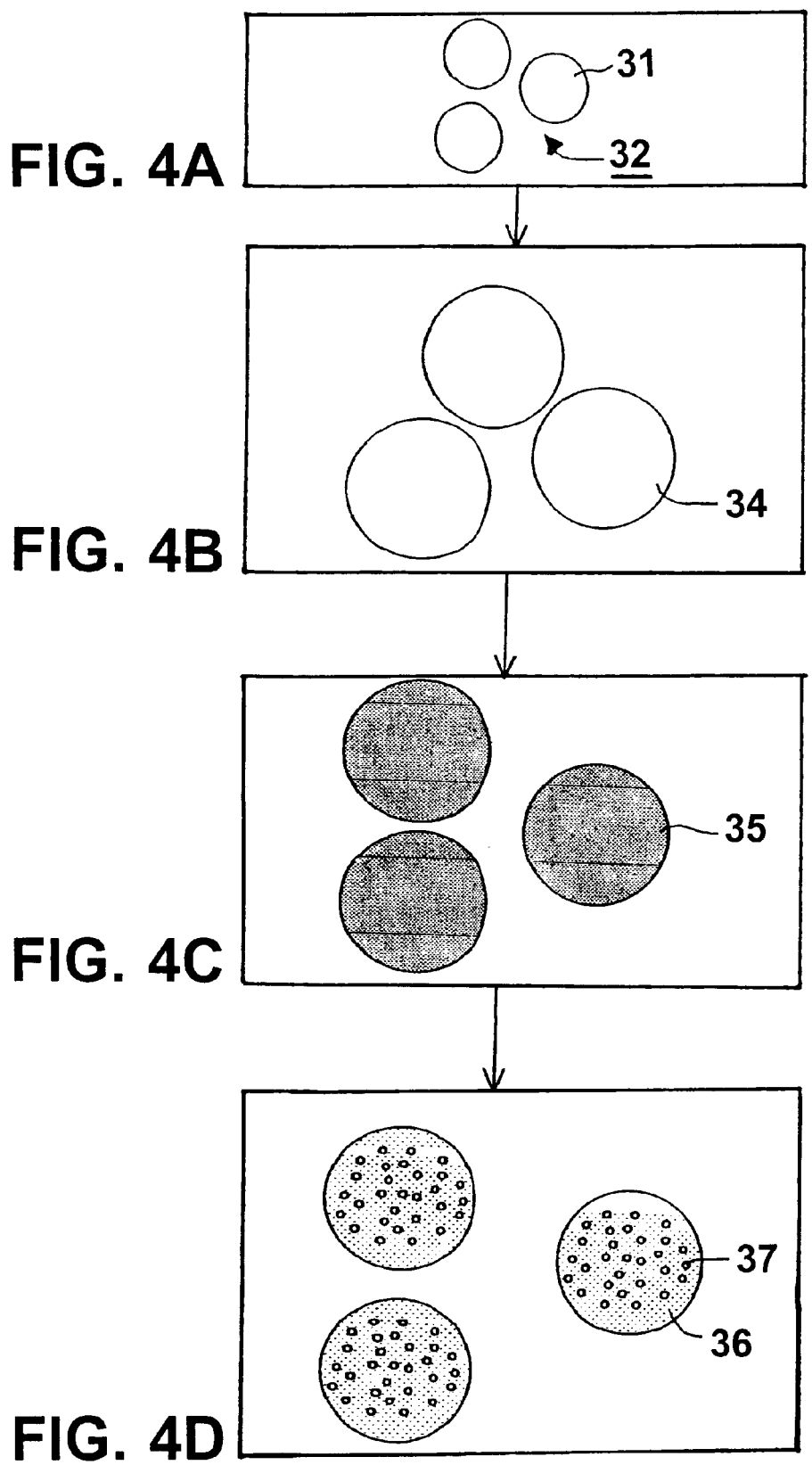

POROUS PARTICLES, POROUS HOLLOW PARTICLES AND METHOD OF PREPARING SUCH PARTICLES

BACKGROUND OF THE INVENTION:

1. Field of the Invention

This invention relates to a method of preparing porous particles and porous hollow particles by forming an emulsion, and to the porous particles and porous hollow particles prepared by this method.

2. Description of the Related Arts

It is known that porous particulates can be prepared by in situ copolymerization and other methods. For example, microcapsules of a copolymer comprising isocyanate may be prepared by in situ copolymerization, and the microcapsules are heated to expand them so as to obtain hydrophilic porous particulates (e.g. Japanese Patent Laid-open Publication no. Hei 1-207133).

However, higher quality porous microcapsules are continually being sought. Good quality porous particles and porous hollow particles may be obtained by a suitable method.

SUMMARY OF THE PRESENT INVENTION

This invention, which was conceived in view of the aforesaid problems, therefore aims to provide higher quality porous particles and by an improved novel preparing method.

The method of preparing porous particles according to this invention comprises:

- a step of preparing a primary emulsion by dispersing a first dispersion phase in a first continuous phase comprising a solidifying component,
- a step of preparing a secondary emulsion by dispersing this primary emulsion in a second continuous phase as a second dispersion phase,
- a step of solidifying the solidifying component in the secondary emulsion, and
- a step of removing the first dispersion phase so as to obtain porous particles.

A method of preparing porous hollow particles according to this invention comprises:

- a step of preparing a primary emulsion by dispersing a first dispersion phase in a first continuous phase comprising a solidifying component,
- a step of preparing a secondary emulsion by dispersing this primary emulsion in a second continuous phase as a second dispersion phase, and
- a step of dissolving a gas under pressure in the first continuous phase of the secondary emulsion, and forming hollow particles by placing the secondary emulsion under ordinary pressure, and
- a step of solidifying the solidifying component, and removing the first dispersion phase so as to obtain porous hollow particles.

Another method of preparing porous hollow particles according to this invention comprises:

- a step of forming hollow particles by placing under ordinary pressure an emulsion comprising a dispersion phase comprising a solidifying component and a gas dissolved under pressure,
- a step of solidifying these solidifying components to a semi-solid state, and impregnating the skins of the hollow particles with a solvent, and
- a step of further solidifying the hollow particles impregnated by solvent, and removing the solvent so as to obtain porous particles.

Another method of forming porous hollow particles according to this invention comprises:

- a step of forming hollow particles by placing under ordinary pressure an emulsion comprising a dispersion phase in which split phase components are blended and a gas is dissolved under pressure,
- a step of solidifying the hollow particles, and
- a step of extracting the split phase components.

The porous particles according to this invention may be prepared by the aforesaid method of preparing porous particles, and the porous hollow particles according to this invention may be prepared by any of the aforesaid methods of preparing porous hollow particles.

BRIEF DESCRIPTION OF THE DRAWINGS

FIG. 3 is a diagram describing steps for preparing porous hollow particles according to this invention comprising steps for impregnating semi-solidified hollow particles with a solvent, further solidifying the hollow particles and removing the solvent.

FIG. 4 is a diagram describing steps for preparing porous hollow particles according to this invention using a split phase method.

DESCRIPTION OF THE PREFERRED EMBODIMENTS OF THE INVENTION

Preparation of Porous Particles

Figures 1A, 1B, 1C, 1D:
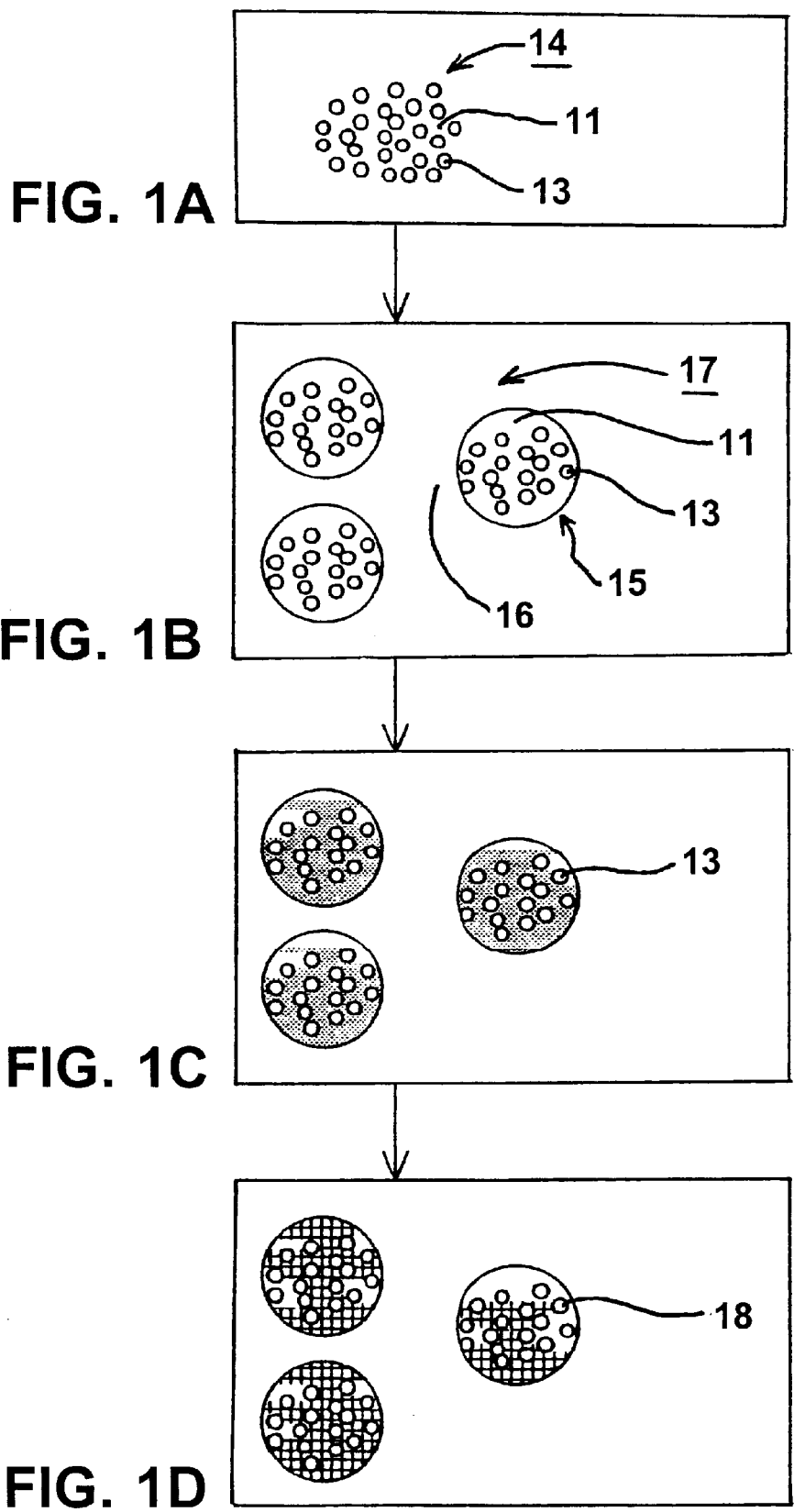
FIG. 1 is a diagram describing the method of preparing porous particles according to this invention.

A primary emulsion 14 (FIG. 1(A)) was prepared by dispersing a first dispersion phase 13 in a first continuous phase 11 comprising a solidifying component. This primary emulsion 14 was dispersed in a second continuous phase 16 as a second dispersion phase 15 so as to obtain a secondary emulsion 17 (FIG. 1(B)). The solidifying component was solidified (FIG. 1(C)), and the first dispersion phase 13 was removed (FIG. 2(D)) to obtain porous particles.

According to this method, the porous particles are prepared by hardening the primary emulsion 14 and removing the first dispersion phase 13. Pores 18 are formed in those parts from which the first dispersion phase 13 is removed (FIG. 1(C)–FIG. 1(D)).

Furthermore according to this method, the pore diameter and/or porosity of the porous particles may be adjusted by adjusting the volume ratio of the first dispersion phase and first continuous phase when the primary emulsion is prepared.

In general, when the volume proportion of the dispersion phase is large, the pore diameter of the porous particles obtained increases, and it is known from experiment that the porosity of the porous particles varies depending on the volume ratio of the dispersion phase and the continuous phase.

Moreover according to the above preparation method, the pore diameter and/or porosity of the porous particles may be adjusted by adjusting at least one condition such as concentration of the solidifying component in the first continuous phase, emulsification degree when the primary emulsion is prepared, volume ratio of the first dispersion phase and first continuous phase, composition of the first continuous phase, and type or concentration of salts dissolved in the first dispersion phase.

In this case, when the concentration of a solidifying component dissolved in the continuous phase is small, the pore diameter of the porous particles increases by a proportionate amount. The pore diameter and/or porosity of the porous particles obtained may be adjusted by adjusting at least one condition such as emulsification degree, volume ratio of the dispersion phase and continuous phase, composition of the continuous phase, and type or concentration of salts dissolved in the first dispersion phase.

In the aforesaid preparation method, the first dispersion phase and second continuous phase may be aqueous phases, and the first continuous phase may be an oil phase.

In this case, the primary emulsion is a w/o emulsion wherein a first aqueous phase (referred to hereafter as "internal aqueous phase") is dispersed in an oil phase comprising a solidifying component. The secondary emulsion is therefore a w/o/w emulsion wherein this w/o emulsion is dispersed in a second aqueous phase (referred to hereafter as "external aqueous phase"). When the oil phase is solidified in the w/o/w emulsion as prepared above, and the internal aqueous phase is removed, the internal aqueous phase leaves pores so that porous particles are formed.

According to the aforesaid preparing method, the first dispersion phase and second continuous phase may be oil phases and the first continuous phase may be an aqueous phase.

In this case, the primary emulsion is an o/w emulsion wherein the first oil phase (referred to hereafter as "internal oil phase") is dispersed in an aqueous phase comprising a solidifying component, which is the converse of the emulsion described above. The secondary emulsion is therefore an o/w/o emulsion wherein this o/w emulsion is dispersed in the second oil phase (referred to hereafter as "secondary oil phase"). When the aqueous phase is solidified in the o/w/o emulsion as prepared above and the internal oil phase is then removed, the internal oil phase leaves pores so that porous particles are formed.

The aforesaid emulsions may be prepared by a VIBRO MIXER (Trade Name, Reika Kogyo, e.g. Tokko Hei 2-015247 (Koho), Tokkai Hei 2-293035 (Koho)) which functions by causing stirring blades to vibrate. Alternatively a mixing device based on a porous pipe (e.g. Tokkai Hei 4-265137 (Koho)) may be used, or a mixer as disclosed in Japanese Patent Application Hei 7-340335 may of course be used.

The continuous phase used in making the primary emulsion contains a solidifying component which ultimately solidifies the continuous phase. When the continuous phase is an oil phase, an oil-based monomer such as styrene monomer is dissolved in it (when styrene monomer is solidified, i.e. polymerized, it solidifies to polystyrene). It is preferable that the solvent used in this case be an oil-based organic solvent capable of dissolving the monomer which it is desired to polymerize, e.g. toluene. On the other hand, when the continuous phase is an aqueous phase, it is preferable that the solidifying component dissolved in this aqueous phase be water glass (i.e. a concentrated aqueous solution of sodium silicate) or the like. When water glass is used, the solid finally obtained is silica.

When the primary emulsion is prepared, it is convenient to carry out emulsification by ultrasonic waves. When ultrasonic waves are used to make the primary emulsion, the particle diameter in the dispersion phase can be made extremely small (e.g. of the order of sub-microns).

As the dispersion phase is a substance which ultimately creates the pores in the porous particles, it is important to control its size, and it was therefore very difficult to make the particle diameter uniformly small.

According to this example however, by making an emulsion with ultrasonic waves, it is particularly easy to make the particles in the dispersion phase of the primary emulsion uniformly small, hence the pore diameter of the porous particles which are ultimately obtained is also uniformly small.

The secondary emulsion is prepared according to the same method as that used to make the primary emulsion. In the case described above, a polymerization initiator may also be added to the system, and additives such as emulsifying agents may also be added in making the primary or secondary emulsion as required.

Porous Particles

The porous particles according to this invention are particles prepared by any of the aforesaid methods of preparing porous particles.

When the porous particles are impregnated with a substance for which slow release is desired, slow release particles are formed. Such slow release particles may be prepared not only by impregnating the porous particles with the desired substance for release, but also by first dissolving that desired substance in the first dispersion phase.

In this case, slow release particles prepared by the method in which the substance to be released is first dissolved in the first dispersion phase are also within the scope and spirit of this invention. The porous particles may for example be impregnated by a slow release substance such as a medicine, an agricultural chemical, or a perfume. In particular, when porous particles impregnated by a fertilizer are made of biodegradable plastic, the particles themselves may be used as an agricultural chemical or fertilizer with no adverse effect on the environment.

The porous particles according to this invention may be used for bioreactor support, in particular a fixing enzyme support. They may also be used as an affinity chromatography matrix (or support).

By forming the skin of the porous particles according to this invention from a substance comprising polar functional groups, polarity may be conferred on the particles. These porous particles having polarity may be used as adsorbants. Therefore when the particles are to be used as, for example, positive ion adsorbants, the particle skin may be formed by using a monomer comprising groups having negative polarity such as carboxyl as a hardening component, and then polymerizing the monomer.

Alternatively, carboxyl groups may be introduced by using water glass as a hardening component, and chemically modifying the shell of the hardened silica particles.

Conversely, when the particles are to be used as, for example, negative ion adsorbants, the particle skin may be formed by using a monomer comprising groups having positive polarity such as amino as a hardening component, and then polymerizing the monomer.

Alternatively, amino groups may be introduced by using water glass as hardening component, and chemically modifying the shell of the hardened silica particles.

Preparation of Porous Hollow Particles

1st method

A first method of preparing porous hollow particles will now be described.

Figures 2A, 2B, 2C, 2D:
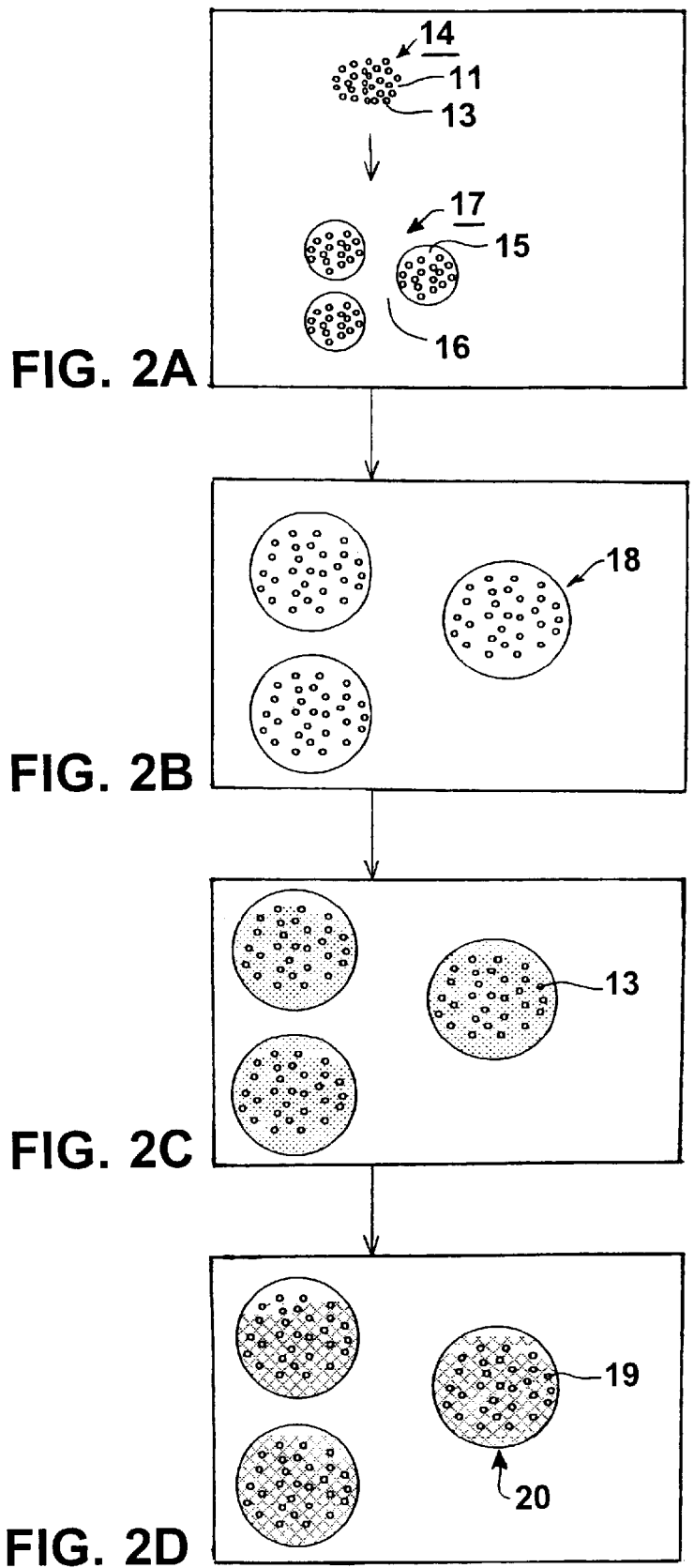
FIG. 2 is a diagram describing steps for preparing porous hollow particles according to this invention using a primary emulsion and a secondary emulsion.

A first dispersion phase 13 is dispersed in a first continuous phase 11 comprising a solidifying component so as to form a primary emulsion 14 (FIG. 2(A)), a gas is dissolved under pressure in the first continuous phase 11, and this primary emulsion 14 is dispersed in a second continuous phase 16 as a second dispersion phase 15 so as to form a secondary emulsion 17 (FIG. 2(B)). This secondary emulsion 17 is then placed under ordinary pressure to form the hollow particles 18 (FIG. 2(C)), the solidifying component is solidified (FIG. 2(D)), and the first dispersion phase 13 is removed (FIG. 2(E)). In this way, porous hollow particles 20 are prepared.

The dissolving of a gas under pressure may be performed before or after making the primary emulsion 14 (Tokkai Hei 5-228359 (Koho)).

2nd Method

Next, a second method of preparing porous hollow particles will be described.

The first dispersion phase 13 is dispersed in the first continuous phase 11 comprising a solidifying component so as to form the primary emulsion 14 (FIG. 2(A)), and this primary emulsion 14 is-dispersed in the second continuous phase 16 as the second dispersion phase 15 so as to form the secondary emulsion 17 (FIG. 2(B)).

A gas is dissolved under pressure in the first continuous phase 11 in this secondary emulsion 17, and the secondary emulsion 17 is placed under ordinary pressure to form the hollow particles 18 (FIG. 2(C)). The solidifying component is solidified (FIG. 2(D)), and the first dispersion phase 13 is removed (FIG. 2(E)). In this way, the porous hollow particles 20 are prepared.

In the above first and second methods, the gas soluble in the first continuous phase described hereafter is chosen according to whether the first continuous phase is an aqueous phase or an oil phase.

In the first and second methods of preparing porous particles according to this invention, the first dispersion phase 13 is removed after hardening the hollow particles 18. The first dispersion phase 13 leaves the pores 19, thereby forming the porous hollow particles 20 (FIG. 2(D)–FIG. 2(E)).

Further, in the above first and second methods of preparing porous hollow particles, the pore diameter and/or porosity of the particles may be adjusted by adjusting the volume ratio of the first dispersion phase and first continuous phase when the primary emulsion is prepared.

In general, when the volume proportion of the dispersion phase is large, the pore diameter of the porous particles obtained increases, and it is known from experiment that the porosity of the porous particles varies depending on the volume ratio of the dispersion phase and the continuous phase.

Moreover, according to the above preparation method, the pore diameter and/or porosity of the porous particles may be adjusted by adjusting at least one condition such as oncentration of a solidifying component in the first tokuecontinuous phase, emulsification degree when the primary emulsion is prepared, volume ratio of the first dispersion phase and first continuous phase, composition of the first continuous phase, and type or concentration of salts dissolved in the first dispersion phase.

In this case, when the concentration of a solidifying component dissolved in the continuous phase is small, the pore diameter of the porous hollow particles increases by a proportionate amount. The pore diameter and/or porosity of the porous particles obtained may be adjusted by adjusting at least one condition such as emulsification degree, volume ratio of the dispersion phase and continuous phase, composition of the continuous phase, or type or concentration of salts dissolved in the first dispersion phase.

In the aforesaid preparation method, the first dispersion phase and second continuous phase may be aqueous phases, and the first continuous phase may be an oil phase.

In this case, the primary emulsion is a w/o emulsion wherein a first aqueous phase (referred to hereafter as "internal aqueous phase") is dispersed in an oil phase comprising a solidifying component. The secondary emulsion is therefore a w/o/w emulsion wherein this w/o emulsion is dispersed in a second aqueous phase (referred to hereafter as "external aqueous phase"). When the oil phase is solidified in the w/o/w emulsion as prepared above, and the internal aqueous phase is removed, the internal aqueous phase leaves pores so that porous hollow particles are formed.

According to the aforesaid preparation method, the first dispersion phase and second continuous phase may be oil phases and the first continuous phase may be an aqueous phase.

In this case, the primary emulsion is an o/w emulsion wherein the first oil phase (referred to hereafter as "internal oil phase") is dispersed in an aqueous phase comprising a solidifying component, which is the converse of the emulsion described above. The secondary emulsion is therefore an o/w/o emulsion wherein this o/w emulsion is dispersed in the second oil phase (referred to hereafter as "secondary oil phase"). When the aqueous phase is solidified in the o/w/o emulsion as prepared above and the internal oil phase is then removed, the internal oil phase leaves pores so that porous particles are formed.

The size of the particles mainly depends on the amount of gas dissolved in the first continuous phase, and their diameter may be freely set in a range from several microns to several millimeters. The particle diameter may be freely controlled also by varying the method used to make the emulsions or adjusting the pressure applied to dissolve the gas. Particles having a diameter outside the above range may therefore be prepared.

3rd method

A third method of preparing porous hollow particles will now be described.

Hollow particles 25 are formed by placing under ordinary pressure an emulsion 24 comprising a solidifying component and a dispersion phase 23 in which a gas is dissolved under pressure (FIG. 3(A)–FIG. 3(B)). These hollow particles 25 are solidified to a semi-solid state (FIG. 3(C)), and the components of the skin of the hollow particles 25 are impregnated by a solvent (FIG. 3(D)). Next, the hollow particles 25 impregnated by solvent are further solidified, and the solvent is removed from the skin so as to leave porous hollow particles (FIG. 3(E)).

The solidifying component may for example be a monomer which is a heat-curing resin. Solidification "to a semi-solid state" when a monomer forming a heat-curing resin is used, is understood to mean polymerization, and "further solidification" after impregnation with solvent is understood to mean solidification due to crosslinking brought about by the action of heat. When another solidifying component is used, the expression "to a semi-solid state" is understood to mean the initial stage of final solidification.

According to this method, the hollow particles are solidified to a semi-solid state (FIG. 3(C)), and the skin of the hollow particles 25 is then impregnated with solvent.

Solvent therefore penetrates the components of the skin which causes the hollow particles to swell by a proportionate amount (FIG. 3(D)). When further solidification is performed, this solidification occurs when solvent has been taken up by the particles.

Consequently when solvent is removed from the solidified hollow particles, spots 26 where solvent had been taken up become cavities, and porous hollow particles 28 are thereby formed. When the solidifying component is polystyrene, the solvent used in this method may be styrene, toluene or ethyl acetate.

4th method

A fourth method of preparing porous hollow particles will now be described.

In the second preparation method, a gas is dissolved under pressure in the first continuous phase 11 of the secondary emulsion 17, the emulsion is solidified to a semi-solid state, and the secondary emulsion 17 is placed under ordinary pressure so as to prepare the hollow particles 18 (FIG. 2(C)). The solidifying component is then further solidified, and the first dispersion phase 13 is removed (FIG. 3(D)) so as to obtain the hollow particles 20.

Herein, the solidifying component may be for example a monomer which is a heat-curing resin. Solidification "to a semi-solid state" when a monomer forming a heat-curing resin is used, is understood to mean polymerization, and "further solidification" after impregnation with solvent is understood to mean solidification due to crosslinking brought about by the action of heat. When another solidifying component is used, the expression "to a semi-solid state" is understood to mean the initial stage of final solidification.

According to this method, the solidifying component is solidified to a semi-solid state, the secondary emulsion 17 is placed under ordinary pressure to swell the solidifying component by a suitable degree, and hollow particles of uniform diameter having a uniform skin are thereby obtained.

5th method

A fifth method of preparing porous hollow particles will now be described.

Hollow particles 34 are formed by placing under ordinary pressure, an emulsion with which a dispersion component has been blended, and which comprises a dispersion phase 31 in which a gas is dissolved under pressure (FIG. 4(A)–FIG.4(B)). These hollow particles 34 are solidified (FIG. 4(C)), and a split phase component is extracted from an emulsion 32 so as to obtain porous hollow particles 36 (FIG. 4(D)).

In this context, the "split phase component" may for example be anhydrous boric acid which is used to prepare porous glass. In general, porous glass is prepared by annealing the glass when anhydrous boric acid is mixed with glass components, and then extracting the anhydrous boric acid by acid treatment.

In the case of this invention, anhydrous boric acid may be mixed with for example water glass (i.e. a concentrated solution of sodium silicate), forming hollow particles by the aforesaid method, and solidifying to form hollow glass particles. Porous hollow glass particles are then prepared by treating these hollow glass particles with acid.

According to this method, when the split phase component of the solidified hollow particles 35 is dissolved, it leaves cavities 37 so that porous hollow particles 36 are formed. In the above case of preparing porous hollow glass particles, the anhydrous boric acid leaves cavities so forming porous hollow glass particles.

The first–fourth methods of preparing porous hollow particles described above make use of a technique disclosed in Tokkai Hei 5-228359 (Koho). According to this technique, a gas is first dissolved under pressure, and, when the pressure is reduced, the gas forms bubbles inside the particles so that balloon-like hollow particles are formed. According to this invention when the first dispersion phase of the primary emulsion is an aqueous phase, after forming the hollow particles, polymerization is carried out followed by drying so as to remove the aqueous phase. The aqueous phase leaves pores so that porous hollow particles are formed. On the other hand, when the first dispersion of the primary emulsion is an oil phase, after forming the hollow particles, polymerization is carried out followed by impregnation with a solvent to dissolve the oil phase and extract it. The oil phase then leaves pores so that porous hollow particles are formed.

Herein, when the primary emulsion is prepared and the first continuous phase is an aqueous phase, it is preferred to use a gas such as carbon dioxide which dissolves easily in the aqueous phase but not very well in the oil phase. On the other hand when the first continuous phase of the primary emulsion is an oil phase, it is preferred to use a gas such as nitrogen which dissolves easily in the oil phase but not very well in the aqueous phase.

The aforesaid emulsions may be prepared by a VIBRO MIXER (Trade Name, Reika Kogyo, e.g. Tokko Hei 2-015247 (Koho), Tokkai Hei 2-293035 (Koho)) which functions by causing stirring blades to vibrate. Alternatively, a mixing device based on a porous pipe (e.g. Tokkai Hei 4-265137 (Koho)) may be used, or a mixer as disclosed in Japanese Patent Application Hei 7-340335 may also of course, be used.

The continuous phase used in making the primary emulsion contains a solidifying component which ultimately solidifies the continuous phase. When the continuous phase is such as styrene monomer dissolved in oil phase, an oil-based monomer is dissolved in it (when styrene monomer is solidified, i.e. polymerized, this solidifies to polystyrene). It is preferable that the solvent used in this case be an oil-based organic solvent able to dissolve the monomer which it is desired to polymerize, e.g. toluene. On the other hand, when the continuous phase is an aqueous phase, it is preferred that the solidifying component dissolved in this aqueous phase is water glass (i.e. a concentrated aqueous solution of sodium silicate) or the like. When the compound is water glass, the solid finally obtained is silica.

When the primary emulsion is prepared, it is convenient to carry out emulsification by ultrasonic waves. When ultrasonic waves are used to make the primary emulsion, the particle diameter in the dispersion phase can be made very small (e.g. of the order of sub-microns).

As the dispersion phase is a substance which ultimately creates the pores in the porous particles, it is important to control its size, and it was therefore very difficult to make the particle diameter uniformly small.

According to this example, however, by making an emulsion with ultrasonic waves, it is particularly easy to make the particles in the dispersion phase of the primary emulsion uniformly small, hence the pore diameter of the porous particles which are ultimately obtained is also uniformly small.

The secondary emulsion is prepared according to the same method as that used to make the primary emulsion. In the case described above, a polymerization initiator may also be added to the system, and additives such as emulsifying agents may also be added in making the primary or secondary emulsion as required.

Figure 5:
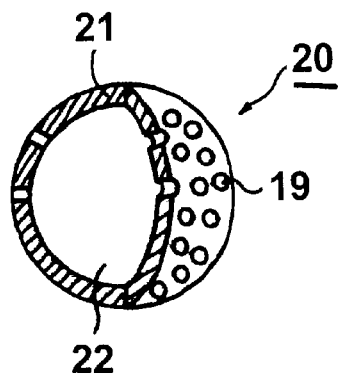
FIG. 5 is a partial cut-away diagram of a porous hollow particle prepared by the aforesaid methods of preparing porous hollow particles according to this invention.
Figure 6:
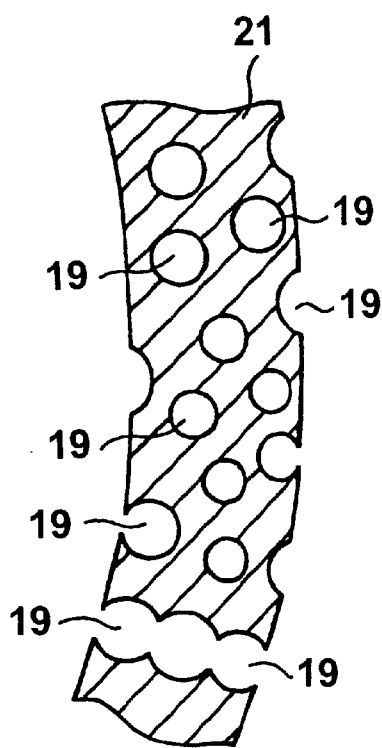
FIG. 6 is an enlarged view in section of a porous hollow particle prepared by the aforesaid methods of preparing porous hollow particles according to this invention.

As shown in FIG. 5, the porous hollow particle 20 comprises a skin 21 forming the shell of the particle, and a hollow part 22 inside the particle. The pores 19 are formed in the skin 21. As shown in FIG. 6, the pores 19 may be embedded in the skin 21, appear only on the surface of the skin 21, appear only inside the hollow part 22, or run right through the skin 21 so as to connect the hollow part 22 with the outside.

As shown in FIG. 6, it may occur that some of the pores 19 are separate while some may run into each other forming cavities (sponge). By setting the preparation conditions as desired, the shape of the pores 19 and their arrangement may be controlled. The preparation conditions may be determined according to the type of use envisaged, e.g. mode of slow release. It should be noted that when the pores 19 are separate, substances are slowly released through the skin of the hollow particle. On the other hand, when the pores form cavities (i.e. when the pores 19 run into each other), substances are released through the cavities.

Porous hollow particles

The porous hollow particles according to this invention are porous hollow particles prepared by the first to fifth methods of preparing porous hollow particles.

When the porous particles are impregnated by a substance which it is desired to release slowly, slow release particles are formed. Such slow release particles may be prepared not only by impregnating the porous particles with the substance it is desired to release, but also by first dissolving the desired substance in the first dispersion phase. In this case, slow release particles prepared by the method in which the substance to be released is first dissolved in the first dispersion phase are also within the scope and spirit of this invention. The porous hollow particles may, for example, be impregnated by a slow release substance such as a medicine, agricultural chemical or perfume. In particular, when porous hollow particles impregnated by a fertilizer are made of a biodegradable plastic, the particles themselves may be used as an agricultural chemical or fertilizer, and they have no adverse effect on the environment.

The porous hollow particles according to this invention may be used as a bioreactor support, in particular a fixing enzyme support. They may also be used as an affinity chromatography matrix (or support).

By forming the skin of the porous hollow particles according to this invention from a substance comprising polar functional groups, polarity may be conferred on the particles. These porous hollow particles having polarity may be used as adsorbants. Therefore when the particles are to be used as, for example, positive ion adsorbants, the particle skin may be formed by using a monomer comprising groups having negative polarity such as carboxyl as a hardening component, and thenpolymerizing the monomer. Alternatively, carboxyl groups may be introduced by using water glass as a hardening component and chemically modifying the skin of the hardened silica particles. Conversely, when the particles are to be used as, for example, negative ion adsorbants, the particle skin may be formed by using a monomer comprising groups having positive polarity such as amino as a hardening component, and then polymerizing the monomer. Alternatively, amino groups may be introduced by using water glass as hardening component, and chemically modifying the skin of the hardened silica particles.

DESCRIPTION OF THE ACTUAL EXAMPLES

Some examples of porous particles will now be described, but it should be understood that the invention is in no way limited to these examples.

The porous particles were prepared according to the conditions shown in Table 1.

Figure 7:
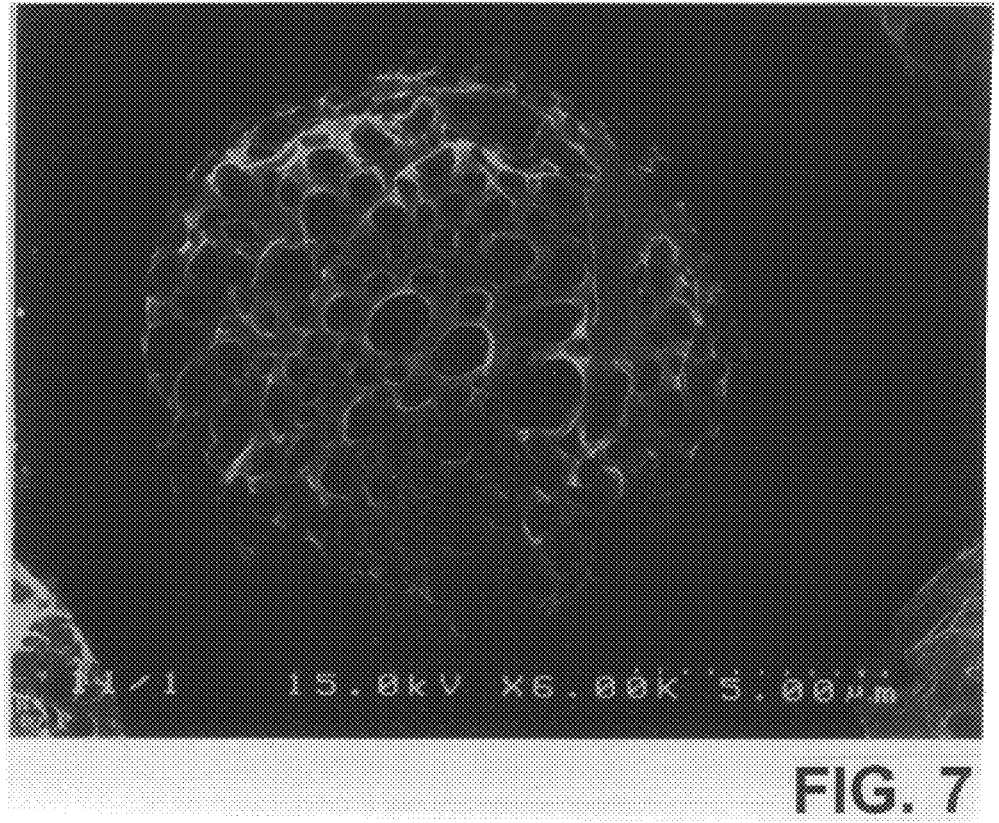
FIG. 7 is an electron micrograph showing the external appearance of a porous particle obtained according to this invention.
Figure 8:
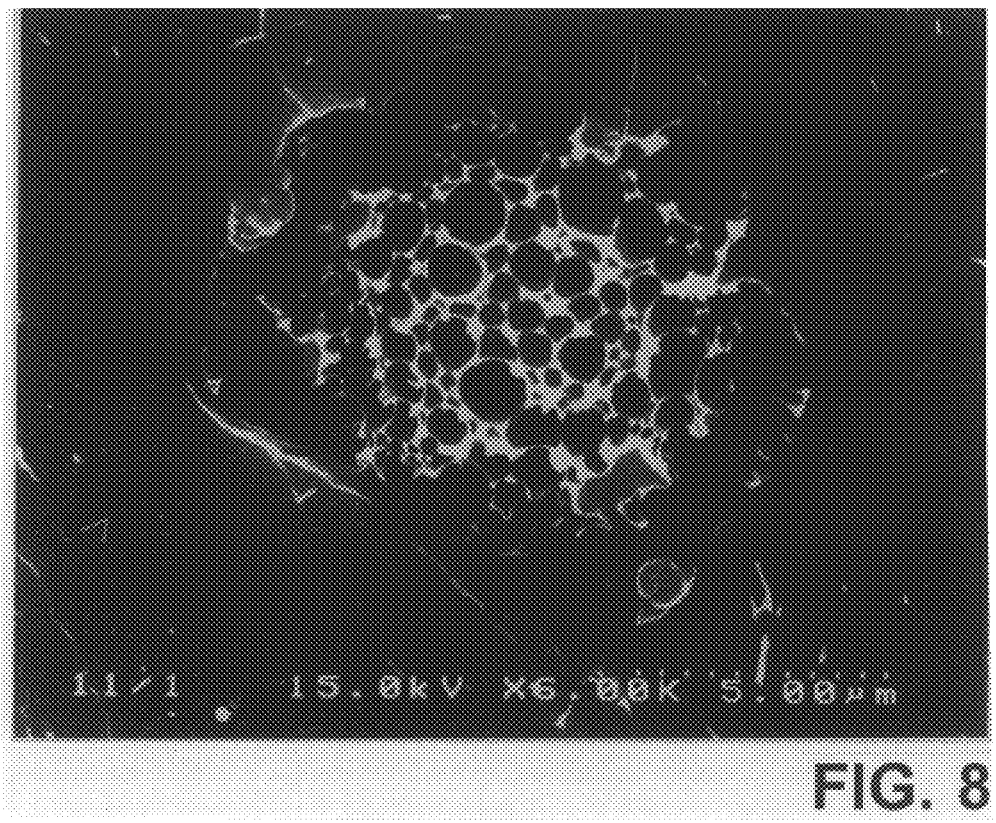
FIG. 8 is an electron micrograph showing a section of a porous particle obtained according to this invention.

Electron micrographs showing the external appearance of and a section through the porous particles obtained are shown in FIG. 7 and FIG. 8.

TABLE 1

| preparing conditions for microcapsule in photograph. | |
|---|---|
| Component | Amount |
| *Internal aqueous phase | |
| $KNO_3$ | 2.0 mol/l |
| *Oil phase | |
| Styrene monomer (wall material) | 3.5 mol/l |
| Divinylbenzene (DVB) (crosslinking agent) | 3.5 mol/l |
| Toluene | 0.95 mol/l |
| Sunsoft 818SX (surfactant) | 0.9 mt% |
| 2,2-Azobis(2,4-dimethylvalernitrile) (ADVN) (Initiator:) | 0.9 mt% |
| *External aqueous phase | |
| Polyvinyl alcohol (PVA) (dispersion stabilizer) | 2.0 wt% |
| Sodium dodecyl sulfate (SDS) (surfactant) | 0.25 wt% |

*Volum ratio
Internal aqueous phase:oil phase = 1:9
Primary emulsion:external aqueous phase = 1:9

(CAPTION TO TABLE 1)

From their external appearance and section, it was found that the porous particles and porous hollow particles according to this invention were effectively spherical, had high porosity, and were of good quality. The size of the particles depends on the amount of primary emulsion. The diameter of the porous particles and hollow porous particles prepared by the method of this invention could be freely set within a range of from several microns to several tens of microns. However, by freely controlling the emulsion preparation conditions, particles having diameters outside this range can be prepared. It is moreover possible to produce pores separate from each other or pores linked to each other forming cavities. Whichever of these options is selected depends on the type of slow release desired from the particles.

As described hereabove, this invention provides a novel method of preparing porous particles and porous hollow particles. The porous particles and porous hollow particles thereby obtained are of good quality, and are expected to have application in a wide variety of fields such as medicine, etc.

What is claimed is:

1. A method of preparing porous particles by:

dispersing a first dispersion phase in a first continuous phase containing a solidifying component so as to prepare a primary emulsion, wherein the solidifying component is an oil-based monomer when the first continuous phase is an oil phase and is a water soluble silicate when the first continuous phase is an aqueous phase;

dispersing said primary emulsion in a second continuous phase as a second dispersion phase so as to prepare a secondary emulsion, solidifying said solidifying component in said secondary emulsion, and then removing said first dispersion phase, wherein the method is carried out by a mixing device selected from the group consisting of devices functioning with vibrating stirring blades and devices based on a porous pipe.

2. A method of preparing porous particles as defined in claim 1, wherein:

the pore diameter and/or porosity of said porous particles is adjusted by adjusting the volume ratio of said first dispersion phase and said first continuous phase when preparing said primary emulsion.

3. A method of preparing porous particles as defined in claim 1, wherein:

the pore diameter and/or porosity of said porous particles is adjusted by adjusting at least one condition comprising the concentration of said solidifying component dissolved in said first continuous phase, the emulsification degree when preparing said primary emulsion, the volume ratio of said first dispersion phase and said first continuous phase, the composition of said first continuous phase, and the type or concentration of salts dissolved in said first dispersion phase.

4. A method of preparing porous hollow particles, said method comprising:

dispersing a first dispersion phase in a first continuous phase containing a solidifying component and dissolving a gas under pressure in said first continuous phase so as to prepare a primary emulsion, wherein the solidifying component is an oil-based monomer when the first continuous phase is an oil phase and is a water soluble silicate when the first continuous phase is an aqueous phase;

dispersing said primary emulsion in a second continuous phase as a second dispersion phase so as to prepare a secondary emulsion;

forming hollow particles by placing said secondary emulsion under ordinary pressure, solidifying said solidifying component; and removing said first dispersion phase, wherein the method is carried out by a mixing device selected from the group consisting of devices functioning with vibrating stirring blades and devices based on a porous pipe.

5. A method of preparing porous hollow particles as defined in claim 4, wherein:

the pore diameter and/or porosity of said porous particles is adjusted by adjusting the volume ratio of said first dispersion phase and said first continuous phase when preparing said primary emulsion.

6. A method of preparing porous hollow particles as defined in claim 4, wherein:

the pore diameter and/or porosity of said porous hollow particles is adjusted by adjusting at least one condition comprising the concentration of said solidifying component dissolved in said first continuous phase, the emulsification degree when preparing said primary emulsion, the volume ratio of said first dispersion phase and said first continuous phase, the composition of said first continuous phase, and the type or concentration of salts dissolved in said first dispersion phase.

7. A method of preparing porous hollow particles, said method comprising:

dispersing a first dispersion phase in a first continuous phas containing a solidifying component so as to prepare a primary emulsion, wherein the solidifying component is an oil-based monomer when the first continuous phase is an oil phase and is a water soluble silicate when the first continuous phase is an aqueous phase;

dispersing said primary emulsion in a second continuous phase as a second dispersion phase so as to prepare a secondary emulsion;

forming hollow particles by dissolving a gas under pressure in said first continuous phase in said secondary emulsion, placing said secondary emulsion under ordinary pressure, solidifying said solidifying component; and removing said first dispersion phase, wherein the method is carried out by a mixing device selected from the group consisting of devices functioning with vibrating stirring blades and devices based on a porous pipe.

8. A method of preparing porous hollow particles as defined in claim 7, wherein:

the pore diameter and/or porosity of said porous hollow particles is adjusted by adjusting the volume ratio of said first dispersion phase and said first continuous phase when preparing said primary emulsion.

9. A method of preparing porous hollow particles as defined in claim 7, wherein:

the pore diameter and/or porosity of said porous particles is adjusted by adjusting at least one condition comprising the concentration of said solidifying component dissolved in said first continuous phase, the emulsification degree when preparing said primary emulsion, the volume ratio of said first dispersion phase and said first continuous phase, the composition of said first continuous phase, and the type or concentration of salts dissolved in said first dispersion phase.

10. A method of preparing porous hollow particles as defined in claim 7, wherein:

a gas is dissolved under pressure in said first continuous phase in said secondary emulsion, said solidifying component is solidified to a semi-solid state, said secondary emulsion is placed under ordinary pressure, said solidifying component is further solidified, and said first dispersion phase of said primary emulsion is then removed.

11. A method of preparing porous particles, said method comprising:

forming hollow particles by placing under ordinary pressure an emulsion comprising a dispersion phase containing a solidifying component and a gas dissolved under pressure, wherein the solidifying component is an oil-based monomer when the first continuous phase is an oil phase and is a water soluble silicate when the first continuous phase is an aqueous phase;

solidifying said solidifying component to a semi-solid state, and the skin of said hollow particles is impregnated by a solvent;

further solidifying said hollow particles impregnated by said solvent; and removing said solvent, wherein the method is carried out by a mixing device selected from the group consisting of devices functioning with vibrating stirring blades and devices based on a porous pipe.

12. A method of preparing porous particles, said method comprising:

forming hollow particles by placing under ordinary pressure an emulsion comprising a dispersion phase containing a solidifying component and a gas dissolved under pressure, wherein the solidifying component is an oil-based monomer when the first continuous phase is an oil phase and is a water soluble silicate when the first continuous phase is an aqueous phase;

solidifying said hollow particles; and, eluting said dispersion phase, wherein the method is carried out by a mixing device selected from the group consisting of devices functioning with vibrating stirring blades and devices based on a porous pipe.

13. Porous particles prepared according to the method of preparing porous particles defined in claim 1.

14. Porous hollow particles prepared according to the method of preparing porous hollow particles defined in claim 4.

15. Porous hollow particles prepared according to the method of preparing porous hollow particles defined in claim 7.

16. Porous particles prepared according to the method of preparing porous particles defined in claim 11.

17. Porous particles prepared according to the method of preparing porous particles defined in claim 12.

18. Slow release particles formed by impregnating the porous particles defined in claim 13 by a substance which it is desired to release slowly.

19. Slow release particles formed by impregnating the porous hollow particles defined in claim 14 by a substance which it is desired to release slowly.

20. A method wherein the porous particles defined in claim 13 are used as a bioreactor support.

* * * * *